(12) United States Patent
Abolfathi

(10) Patent No.: US 9,143,873 B2
(45) Date of Patent: *Sep. 22, 2015

(54) METHODS AND APPARATUS FOR TRANSMITTING VIBRATIONS

(71) Applicant: Sonitus Medical, Inc., San Mateo, CA (US)

(72) Inventor: Amir A. Abolfathi, Woodside, CA (US)

(73) Assignee: Sonitus Medical, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/056,806

(22) Filed: Oct. 17, 2013

(65) Prior Publication Data

US 2014/0275733 A1    Sep. 18, 2014

Related U.S. Application Data

(63) Continuation of application No. 13/471,162, filed on May 14, 2012, now Pat. No. 8,585,575, which is a continuation of application No. 12/940,783, filed on Nov. 5, 2010, now Pat. No. 8,177,705, which is a (Continued)

(51) Int. Cl.
*H04R 25/00* (2006.01)
*A61C 8/00* (2006.01)

(52) U.S. Cl.
CPC ............ *H04R 25/554* (2013.01); *H04R 25/604* (2013.01); *H04R 25/606* (2013.01); *A61C 8/0075* (2013.01); *H04R 25/75* (2013.01); *H04R 2420/07* (2013.01); *H04R 2460/13* (2013.01)

(58) Field of Classification Search
CPC .... H04R 25/00; H04R 25/554; H04R 25/604; H04R 25/606

USPC ........ 600/23–25; 381/312–331; 181/126–137
See application file for complete search history.

(56) References Cited

U.S. PATENT DOCUMENTS 2,045,404 A   6/1936   Nicholides
2,161,169 A   6/1939   Jefferis (Continued)

FOREIGN PATENT DOCUMENTS

DE   30 30 132 A1   3/1982
EP   0715838 A2     6/1996

(Continued)

OTHER PUBLICATIONS

Altmann, et al. Foresighting the new technology waves—Exper Group. In: State of the Art Reviews and Related Papers—Center on Nanotechnology and Society. 2004 Conference. Published Jun. 14, 2004. p. 1-291. Available at http://www.nano-and-society.org/NELSI/documents/ECreviewsandpapers061404.pdf. Accessed Jan. 11, 2009.

(Continued)

*Primary Examiner* — John Lacyk
(74) *Attorney, Agent, or Firm* — Levine Bagade Han LLP

(57) ABSTRACT

Methods and apparatus for transmitting vibrations via an electronic and/or transducer assembly through a dental implant are disclosed herein. The assembly may be attached, adhered, or otherwise embedded into or upon the implant to form a hearing assembly. The electronic and transducer assembly may receive incoming sounds either directly or through a receiver to process and amplify the signals and transmit the processed sounds via a vibrating transducer element coupled to a tooth or other hone structure, such as the maxillary, mandibular, or palatine bone structure.

20 Claims, 13 Drawing Sheets

Related U.S. Application Data continuation of application No. 12/726,982, filed on Mar. 18, 2010, now Pat. No. 7,854,698, which is a continuation of application No. 11/866,345, filed on Oct. 2, 2007, now Pat. No. 7,682,303.

(56) References Cited

U.S. PATENT DOCUMENTS

| | | |
|---|---|---|
| 2,230,397 A | 2/1941 | Abraham |
| 2,242,118 A | 5/1941 | Fischer |
| 2,318,872 A | 5/1943 | Madiera |
| 2,977,425 A | 3/1961 | Cole |
| 2,995,633 A | 8/1961 | Puharich et al. |
| 3,156,787 A | 11/1964 | Puharich et al. |
| 3,170,993 A | 2/1965 | Puharich et al. |
| 3,267,931 A | 8/1966 | Puharich et al. |
| 3,325,743 A | 6/1967 | Blum |
| 3,712,962 A | 1/1973 | Epley |
| 3,787,641 A | 1/1974 | Santori |
| 3,894,196 A | 7/1975 | Briskey |
| 3,985,977 A | 10/1976 | Beaty et al. |
| 4,025,732 A | 5/1977 | Traunmuller |
| 4,150,262 A | 4/1979 | Ono |
| 4,498,461 A | 2/1985 | Hakansson |
| 4,591,668 A | 5/1986 | Iwata |
| 4,612,915 A | 9/1986 | Hough et al. |
| 4,642,769 A | 2/1987 | Petrofsky |
| 4,738,268 A | 4/1988 | Kipnis |
| 4,791,673 A | 12/1988 | Schreiber |
| 4,817,044 A | 3/1989 | Ogren |
| 4,832,033 A | 5/1989 | Maher et al. |
| 4,920,984 A | 5/1990 | Furumichi et al. |
| 4,962,559 A | 10/1990 | Schuman |
| 4,982,434 A | 1/1991 | Lenhardt et al. |
| 5,012,520 A | 4/1991 | Steeger |
| 5,033,999 A | 7/1991 | Mersky |
| 5,047,994 A | 9/1991 | Lenhardt et al. |
| 5,060,526 A | 10/1991 | Barth et al. |
| 5,082,007 A | 1/1992 | Adell |
| 5,233,987 A | 8/1993 | Fabian et al. |
| 5,323,468 A | 6/1994 | Bottesch |
| 5,325,436 A | 6/1994 | Soli et al. |
| 5,354,326 A | 10/1994 | Comben et al. |
| 5,372,142 A | 12/1994 | Madsen et al. |
| 5,402,496 A | 3/1995 | Soli et al. |
| 5,403,262 A | 4/1995 | Gooch |
| 5,447,489 A | 9/1995 | Issalene et al. |
| 5,455,842 A | 10/1995 | Merskey et al. |
| 5,460,593 A | 10/1995 | Mersky et al. |
| 5,477,489 A | 12/1995 | Wiedmann |
| 5,546,459 A | 8/1996 | Sih et al. |
| 5,558,618 A | 9/1996 | Maniglia |
| 5,565,759 A | 10/1996 | Dunstan |
| 5,579,284 A | 11/1996 | May |
| 5,616,027 A | 4/1997 | Jacobs et al. |
| 5,624,376 A | 4/1997 | Ball et al. |
| 5,661,813 A | 8/1997 | Shimauchi et al. |
| 5,706,251 A | 1/1998 | May |
| 5,735,790 A | 4/1998 | Hakansson et al. |
| 5,760,692 A | 6/1998 | Block |
| 5,800,336 A | 9/1998 | Ball et al. |
| 5,812,496 A | 9/1998 | Peck |
| 5,828,765 A | 10/1998 | Gable |
| 5,902,167 A | 5/1999 | Filo et al. |
| 5,914,701 A | 6/1999 | Gersheneld et al. |
| 5,961,443 A | 10/1999 | Rastatter et al. |
| 5,984,681 A | 11/1999 | Huang |
| 6,029,558 A | 2/2000 | Stevens et al. |
| 6,047,074 A | 4/2000 | Zoels et al. |
| 6,057,668 A | 5/2000 | Chao |
| 6,068,590 A | 5/2000 | Brisken |
| 6,072,884 A | 6/2000 | Kates |
| 6,072,885 A | 6/2000 | Stockham, Jr. et al. |
| 6,075,557 A | 6/2000 | Holliman et al. |
| 6,089,864 A | 7/2000 | Buckner et al. |
| 6,115,477 A | 9/2000 | Filo et al. |
| 6,118,882 A | 9/2000 | Haynes |
| 6,171,229 B1 | 1/2001 | Kroll et al. |
| 6,223,018 B1 | 4/2001 | Fukumoto et al. |
| 6,239,705 B1 | 5/2001 | Glen |
| 6,333,269 B2 | 12/2001 | Naito et al. |
| 6,371,758 B1 | 4/2002 | Kittelsen |
| 6,377,693 B1 | 4/2002 | Lippa et al. |
| 6,394,969 B1 | 5/2002 | Lenhardt |
| 6,504,942 B1 | 1/2003 | Hong et al. |
| 6,538,558 B2 | 3/2003 | Sakazume et al. |
| 6,585,637 B2 | 7/2003 | Brillhart et al. |
| 6,629,922 B1 | 10/2003 | Puria et al. |
| 6,631,197 B1 | 10/2003 | Taenzer |
| 6,633,747 B1 | 10/2003 | Reiss |
| 6,658,124 B1 | 12/2003 | Meadows |
| 6,682,472 B1 | 1/2004 | Davis |
| 6,694,035 B1 | 2/2004 | Teicher et al. |
| 6,754,472 B1 | 6/2004 | Williams et al. |
| 6,778,674 B1 | 8/2004 | Panasik et al. |
| 6,826,284 B1 | 11/2004 | Benesty et al. |
| 6,885,753 B2 | 4/2005 | Bank |
| 6,917,688 B2 | 7/2005 | Yu et al. |
| 6,941,952 B1 | 9/2005 | Rush, III |
| 6,954,668 B1 | 10/2005 | Cuozzo |
| 6,985,599 B2 | 1/2006 | Asnes |
| 7,003,099 B1 | 2/2006 | Zhang et al. |
| 7,010,139 B1 | 3/2006 | Smeehuyzen |
| 7,033,313 B2 | 4/2006 | Lupin et al. |
| 7,035,415 B2 | 4/2006 | Belt et al. |
| 7,065,223 B2 | 6/2006 | Westerkull |
| 7,074,222 B2 | 7/2006 | Westerkull |
| 7,076,077 B2 | 7/2006 | Atsumi et al. |
| 7,099,822 B2 | 8/2006 | Zangi |
| 7,162,420 B2 | 1/2007 | Zangi et al. |
| 7,171,003 B1 | 1/2007 | Venkatesh et al. |
| 7,171,008 B2 | 1/2007 | Elko |
| 7,174,022 B1 | 2/2007 | Zhang et al. |
| 7,174,026 B2 | 2/2007 | Niederdränk |
| 7,198,596 B2 | 4/2007 | Westerkull |
| 7,206,423 B1 | 4/2007 | Feng et al. |
| 7,246,058 B2 | 7/2007 | Burnett |
| 7,258,533 B2 | 8/2007 | Tanner et al. |
| 7,269,266 B2 | 9/2007 | Anjanappa et al. |
| 7,271,569 B2 | 9/2007 | Oglesbee |
| 7,310,427 B2 | 12/2007 | Retchin et al. |
| 7,329,226 B1 | 2/2008 | Ni et al. |
| 7,331,349 B2 | 2/2008 | Brady et al. |
| 7,333,624 B2 | 2/2008 | Husung |
| 7,361,216 B2 | 4/2008 | Kangas et al. |
| 7,409,070 B2 | 8/2008 | Pitulia |
| 7,486,798 B2 | 2/2009 | Anjanappa et al. |
| 7,520,851 B2 | 4/2009 | Davis et al. |
| 7,522,738 B2 | 4/2009 | Miller, III |
| 7,522,740 B2 | 4/2009 | Julstrom et al. |
| 7,664,277 B2 | 2/2010 | Abolfathi et al. |
| 7,682,303 B2 | 3/2010 | Abolfathi |
| 7,724,911 B2 | 5/2010 | Menzel et al. |
| 7,796,769 B2 | 9/2010 | Abolfathi |
| 7,854,698 B2 | 12/2010 | Abolfathi |
| 8,177,705 B2 | 5/2012 | Abolfathi |
| 8,585,575 B2 | 11/2013 | Abolfathi |
| 2001/0003788 A1 | 6/2001 | Ball et al. |
| 2001/0051776 A1 | 12/2001 | Lenhardt |
| 2002/0026091 A1 | 2/2002 | Leysieffer |
| 2002/0071581 A1 | 6/2002 | Leysieffer et al. |
| 2002/0077831 A1 | 6/2002 | Numa |
| 2002/0122563 A1 | 9/2002 | Schumaier |
| 2002/0173697 A1 | 11/2002 | Lenhardt |
| 2003/0048915 A1 | 3/2003 | Bank |
| 2003/0059078 A1 | 3/2003 | Downs et al. |
| 2003/0091200 A1 | 5/2003 | Pompei |
| 2003/0212319 A1 | 11/2003 | Magill |
| 2004/0057591 A1 | 3/2004 | Beck et al. |
| 2004/0063073 A1 | 4/2004 | Kajimoto et al. |
| 2004/0131200 A1 | 7/2004 | Davis |
| 2004/0141624 A1 | 7/2004 | Davis et al. |
| 2004/0202339 A1 | 10/2004 | O'Brien, Jr. et al. |
| 2004/0202344 A1 | 10/2004 | Anjanappa et al. |

(56) References Cited

U.S. PATENT DOCUMENTS

| | | |
|---|---|---|
| 2004/0243481 A1 | 12/2004 | Bradbury et al. |
| 2004/0247143 A1 | 12/2004 | Lantrua et al. |
| 2005/0037312 A1 | 2/2005 | Uchida |
| 2005/0067816 A1 | 3/2005 | Buckman |
| 2005/0070782 A1 | 3/2005 | Brodkin |
| 2005/0129257 A1 | 6/2005 | Tamura |
| 2005/0189910 A1 | 9/2005 | Hui |
| 2005/0196008 A1 | 9/2005 | Anjanappa et al. |
| 2005/0241646 A1 | 11/2005 | Sotos et al. |
| 2006/0008106 A1 | 1/2006 | Harper |
| 2006/0025648 A1 | 2/2006 | Lupin et al. |
| 2006/0064037 A1 | 3/2006 | Shalon et al. |
| 2006/0167335 A1 | 7/2006 | Park et al. |
| 2006/0207611 A1 | 9/2006 | Anonsen |
| 2006/0270467 A1 | 11/2006 | Song et al. |
| 2006/0275739 A1 | 12/2006 | Ray |
| 2007/0010704 A1 | 1/2007 | Pitulia |
| 2007/0035917 A1 | 2/2007 | Hotelling et al. |
| 2007/0036370 A1 | 2/2007 | Granovetter et al. |
| 2007/0041595 A1 | 2/2007 | Carazo et al. |
| 2007/0142072 A1 | 6/2007 | Lassally |
| 2007/0223735 A1 | 9/2007 | LoPresti et al. |
| 2007/0230713 A1 | 10/2007 | Davis |
| 2007/0242835 A1 | 10/2007 | Davis |
| 2007/0265533 A1 | 11/2007 | Tran |
| 2007/0276270 A1 | 11/2007 | Tran |
| 2007/0280491 A1 | 12/2007 | Abolfathi |
| 2007/0280492 A1 | 12/2007 | Abolfathi |
| 2007/0280493 A1 | 12/2007 | Abolfathi |
| 2007/0280495 A1 | 12/2007 | Abolfathi |
| 2007/0286440 A1 | 12/2007 | Abolfathi et al. |
| 2007/0291972 A1 | 12/2007 | Abolfathi et al. |
| 2008/0019542 A1 | 1/2008 | Menzel et al. |
| 2008/0019557 A1 | 1/2008 | Bevirt et al. |
| 2008/0021327 A1 | 1/2008 | El-Bialy et al. |
| 2008/0064993 A1 | 3/2008 | Abolfathi et al. |
| 2008/0070181 A1 | 3/2008 | Abolfathi et al. |
| 2008/0109972 A1 | 5/2008 | Mah et al. |
| 2008/0205678 A1 | 8/2008 | Boglavskij et al. |
| 2008/0304677 A1 | 12/2008 | Abolfathi et al. |
| 2009/0028352 A1 | 1/2009 | Petroff |
| 2009/0052698 A1 | 2/2009 | Rader et al. |
| 2009/0088598 A1 | 4/2009 | Abolfathi |
| 2009/0097684 A1 | 4/2009 | Abolfathi et al. |
| 2009/0097685 A1 | 4/2009 | Menzel et al. |
| 2009/0099408 A1 | 4/2009 | Abolfathi et al. |
| 2009/0105523 A1 | 4/2009 | Kassayan et al. |
| 2009/0147976 A1 | 6/2009 | Abolfathi |
| 2009/0149722 A1 | 6/2009 | Abolfathi et al. |
| 2009/0180652 A1 | 7/2009 | Davis et al. |
| 2009/0220115 A1 | 9/2009 | Lantrua |
| 2009/0226020 A1 | 9/2009 | Abolfathi |
| 2010/0185046 A1 | 7/2010 | Abolfathi |
| 2010/0189288 A1 | 7/2010 | Menzel et al. |
| 2011/0245584 A1 | 10/2011 | Abolfathi |
| 2012/0296154 A1 | 11/2012 | Abolfathi |

FOREIGN PATENT DOCUMENTS

| | | |
|---|---|---|
| EP | 0824889 A1 | 2/1998 |
| EP | 1783919 A1 | 5/2007 |
| GB | 1066299 A | 4/1967 |
| JP | 56-026490 | 3/1981 |
| JP | 58-502178 | 12/1983 |
| JP | 62-159099 | 10/1987 |
| JP | 2004-221949 A | 8/2004 |
| JP | 2007028248 A2 | 2/2007 |
| JP | 2007028610 A2 | 2/2007 |
| JP | 2007044284 A2 | 2/2007 |
| JP | 2007049599 A2 | 2/2007 |
| JP | 2007049658 A2 | 2/2007 |
| WO | WO 83/02047 | 6/1983 |
| WO | WO 91/02678 | 3/1991 |
| WO | WO 95/06398 | 3/1995 |
| WO | WO 95/19678 | 7/1995 |
| WO | WO 96/00051 | 1/1996 |
| WO | WO 96/21335 | 7/1996 |
| WO | WO 02/09622 | 2/2002 |
| WO | WO 02/24126 | 3/2002 |
| WO | WO 2004/045242 | 5/2004 |
| WO | WO 2004/105650 | 12/2004 |
| WO | WO 2005/000391 | 1/2005 |
| WO | WO 2005/037153 | 4/2005 |
| WO | WO 2005/053533 | 6/2005 |
| WO | WO 2006/088410 | 8/2006 |
| WO | WO 2006/130909 | 12/2006 |
| WO | WO 2007/043055 | 4/2007 |
| WO | WO 2007/052251 | 5/2007 |
| WO | WO 2007/059185 | 5/2007 |
| WO | WO 2007/140367 | 12/2007 |
| WO | WO 2007/140368 | 12/2007 |
| WO | WO 2007/140373 | 12/2007 |
| WO | WO 2007/143453 | 12/2007 |
| WO | WO 2008/024794 | 2/2008 |
| WO | WO 2008/030725 | 3/2008 |
| WO | WO 2009/014812 | 1/2009 |
| WO | WO 2009/025917 | 2/2009 |
| WO | WO 2009/045598 | 4/2009 |
| WO | WO 2009/066296 | 5/2009 |
| WO | WO 2009/102889 | 8/2009 |
| WO | WO 2009/111404 | 9/2009 |
| WO | WO 2009/111566 | 9/2009 |

OTHER PUBLICATIONS

Berard, G., "Hearing Equals Behavior" [summary], 1993, http://www.bixby.org/faq/tinnitus/treatment.html.

Bozkaya, D. et al., "Mechanics of the Tapered Interference Fit in Dental Implants," published Oct. 2002 [online], retrieved Oct. 14, 2010. http://www1.coe.neu.edu/~smuftu/Papers/paper-interference-fit-elsevier-2.pdf.

Broyhill, D., "Battlefield Medical Information System—Telemedicine," A research paper presented to the U.S. Army Command and General Staff College in partial Fulfillment of the requirement for A462 Combat Health Support Seminar, 12 pages, 2003.

Dental Cements—Premarket Notification, U.S. Department of Health and Human Services Food and Drug Administration Center for Devices and Radiological Health, pp. 1-10, Aug. 18, 1998.

Henry, et al. "Comparson of Custom Sounds for Achieving Tinnitus Relief" *J Am Acad Audiol*,15:585-598, 2004.

Jastreboff, Pawel, J., "Phantom auditory perception (tinnitus): mechanisms of generation and perception," *Neuroscience Research*, 221-254, 1990, Elsevier Scientific Publishers Ireland, Ltd.

Robb, "Tinnitus Device Directory Part I," *Tinnitus Today*, p. 22, Jun. 2003.

Song, S. et al., "A 0.2-mW 2-Mb/s Digital Transceiver Based on Wideband Signaling for Human Body Communications," *IEEE J Solid-State Cir*, 42(9); 2021-2033, Sep. 2007.

"Special Forces Smart Noise Cancellation Ear Buds with Built-In GPS," http://www.gizmag.com/special-forces-smart-noise-cancellation-ear-buds-with-built-in-gps/9428/, 2 pages, 2008.

Stuart, A., et al., "Investigations of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].

Wen, Y. et al, "Online Prediction of Battery Lifetime for Embedded and Mobile Devices," Special Issue on Embedded Systems: Springer-Verlag Heidelberg Lecture Notes in Computer Science, V3164/2004, 15 pages, Dec. 2004.

METHODS AND APPARATUS FOR TRANSMITTING VIBRATIONS

CROSS-REFERENCE TO RELATED APPLICATIONS

This application is a continuation of U.S. patent application Ser. No. 13/471,162 filed May 14, 2012, which is a continuation of U.S. patent application Ser. No. 12/940,783 filed Nov. 5, 2010, now U.S. Pat. No. 8,177,705 issued May 15, 2012, which is a continuation of U.S. patent application Ser. No. 12/726,982 filed Mar. 18, 2010, now U.S. Pat. No. 7,854,698 issued Dec. 21, 2010, which is a continuation of U.S. patent application Ser. No. 11/866,345 filed Oct. 2, 2007, now U.S. Pat. No. 7,682,303 issued Mar. 23, 2010, the contents of which are incorporated herewith by reference in their entirety.

FIELD OF THE INVENTION

The present invention relates to methods and apparatus for transmitting vibrations through teeth or bone structures in and/or around a mouth.

BACKGROUND OF THE INVENTION

Hearing loss affects over 31 million people in the United States (about 13% of the population). As a chronic condition, the incidence of hearing impairment rivals that of heart disease and, like heart disease, the incidence of hearing impairment increases sharply with age.

While the vast majority of those with hearing loss can be helped by a well-fitted, high quality hearing device, only 22% of the total hearing impaired population own hearing devices. Current products and distribution methods are not able to satisfy of reach over 20 million persons with hearing impairment in the U.S. alone.

Hearing loss adversely affects a person's quality of life and psychological well-being. Individuals with hearing impairment often withdraw from social interactions to avoid frustrations resulting from inability to understand conversations. Recent studies have shown that hearing impairment causes increased stress levels, reduced self-confidence, reduced sociability and reduced effectiveness in the workplace.

The human ear generally comprises three regions: the outer ear, the middle ear, and the inner ear. The Outer ear generally comprises the external auricle and the ear canal, which is a tubular pathway through which sound reaches the middle ear. The outer ear is separated from the middle ear by the tympanic membrane (eardrum). The middle ear generally comprises three small bones, known as the ossicles, which form a mechanical conductor from the tympanic membrane to the inner ear. Finally, the inner ear includes the cochlea, which is a fluid-filled structure that contains a large number of delicate sensory hair cells that are connected to the auditory nerve.

Hearing loss can also be classified in terms of being conductive, sensorineural, or a combination of both. Conductive hearing impairment typically results from diseases or disorders that limit the transmission of sound through the middle ear. Most conductive impairments can be treated medically or surgically. Purely conductive hearing loss represents a relatively small portion of the total healing impaired population (estimated at less than 5% of the total hearing impaired population).

Sensorineural hearing losses occur mostly in the inner ear and account for the vast majority of hearing impairment (estimated at 90-95% of the total hearing impaired population). Sensorineural hearing impairment (sometimes called "nerve loss") is largely caused by damage to the sensory hair cells inside the cochlea. Sensorineural hearing impairment occurs naturally as a result of aging or prolonged exposure to loud music and noise. This type of hearing loss cannot be reversed nor can it be medically or surgically treated however, the use of properly fitted hearing devices can improve the individual's quality of life.

Conventional hearing devices are the most common devices used to treat mild to severe sensorineural hearing impairment. These are acoustic devices that amplify sound to the tympanic membrane. These devices are individually customizable to the patient's physical and acoustical characteristics over four to six separate visits to an audiologist or hearing instrument specialist. Such devices generally comprise a microphone, amplifier, battery, and speaker. Recently, hearing device manufacturers have increased the sophistication of sound processing, often using digital technology, to provide features such as programmability and multi-band compression. Although these devices have been miniaturized and are less obtrusive, they are still visible and have major acoustic limitation.

Industry research has shown that the primary obstacles for not purchasing a hearing device generally include: a) the stigma associated with wearing a hearing device: b) dissenting attitudes on the part of the medical profession, particularly ENT physicians; c) product value issues related to perceived performance problems; d) general lack of information and education at the consumer and physician level; and e) negative word-of-mouth from dissatisfied users.

Other devices such as cochlear implants have been developed for people who have severe to profound hearing loss and are essentially deaf (approximately 2% of the total hearing impaired population). The electrode of a cochlear implant is inserted into the inner ear in an invasive and non-reversible surgery. The electrode electrically stimulates the auditory nerve through an electrode array that provides audible cues to the user, which are not usually interpreted by the brain as normal sound. Users generally require intensive and extended counseling and training following surgery to achieve the expected benefit.

Other devices such as electronic middle ear implants generally are surgically placed within the middle ear of the hearing impaired. They are surgically implanted devices with an externally worn component.

The manufacture, fitting and dispensing of hearing devices remain an arcane and inefficient process. Most hearing devices are custom manufactured, fabricated by the manufacturer to fit the ear of each prospective purchaser. An impression of the ear canal is taken by the dispenser (either an audiologist or licensed hearing instrument specialist) and mailed to the manufacturer for interpretation and fabrication of the custom molded rigid plastic casing. Hand-wired electronics and transducers (microphone and speaker) are then placed inside the casing, and the final product is shipped back to the dispensing professional after some period of dim, typically one to two weeks.

The time cycle for dispensing a hearing device, from the first diagnostic session to the final fine-tuning session, typically spans a period over several weeks, such as six to eight weeks, and involves multiple with the dispenser.

Accordingly, there exists a need for methods and devices which are efficacious and safe in facilitating the treatment of hearing loss in patients.

In another trend, more and more dentists and oral surgeons have turned to dental implants as an acceptable and appropriate means to restore a tooth that has been lost because of disease or trauma. Such dental implants offer an attractive alternative to other options because with a dental implant the patient realizes a restoration that closely approximates a natural tooth without having to alter the structure or appearance of adjacent natural teeth which occurs, for example, when a patient chooses a bridge option. U.S. Pat. No. 5,984,681 discloses an implant for insertion into the alveolar bone of a patient and wherein the implant is provided with a generally vertically projecting anchoring pin that extends from the implant into the alveolar bone of the patient and effectively interconnects the implant with the alveolar bone.

SUMMARY OF THE INVENTION

Methods and apparatus for transmitting vibrations via an electronic and/or transducer assembly through an implant are disclosed herein. The assembly may be rigidly attached, adhered, reversibly connected, or otherwise embedded into or upon the implant to form a hearing assembly. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

In one aspect, the apparatus for transmitting vibrations via at least one bone or tissue to facilitate hearing in a patient includes an implant having an implant head and a threaded portion adapted to be positioned below a gum line; and a housing coupled to the implant head and in vibratory communication with the implant head, the housing having an actuatable transducer disposed within or upon the housing.

In another aspect, a method of transmitting vibrations via at least one dental implant includes placing the dental implant on a patient; and positioning an actuatable transducer such that the implant and transducer remain in vibratory communication.

One example of a method for transmitting these vibrations via at least one tooth may generally comprising positioning a housing of the removable oral appliance onto at least one tooth, whereby the housing has a shape which is conformable to at least a portion of the tooth, and maintaining contact between a surface of the tooth with an actuatable transducer such that the surface and transducer remain in vibratory communication.

DETAILED DESCRIPTION OF THE INVENTION

An electronic and transducer device may be attached, adhered, or otherwise embedded into or upon a dental implant appliance to form a hearing aid assembly. Such an oral appliance may be a custom-made dental implant device. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

Figure 1:
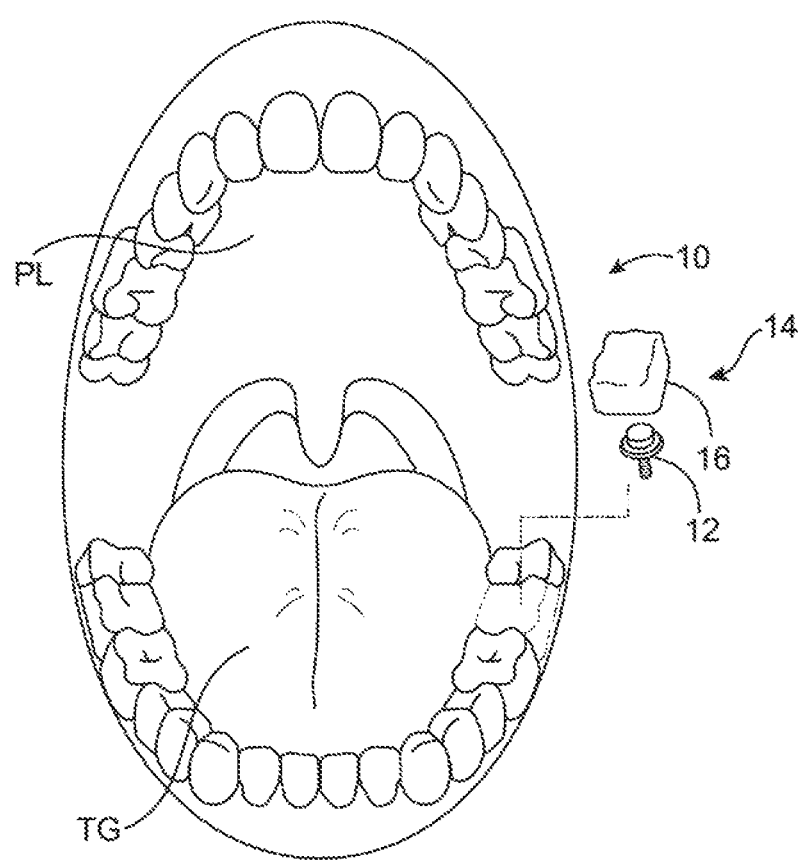
FIG. 1 illustrates the dentition of a patient's teeth and one embodiment of a hearing aid implanted device.

As shown in FIG. 1, a patient's mouth and dentition 10 is illustrated showing one possible location for removably attaching hearing aid assembly 14 upon or against at least one implant 12 connected to bone or tissues or one tooth, such as a dental screw 12. The patient's tongue TG and palate PL are also illustrated for reference. An electronics and/or transducer assembly 16 may be attached, adhered, or otherwise embedded into or upon the assembly 14 using magnetic, mechanical, or chemical attachment as described below in further detail.

Figure 2:
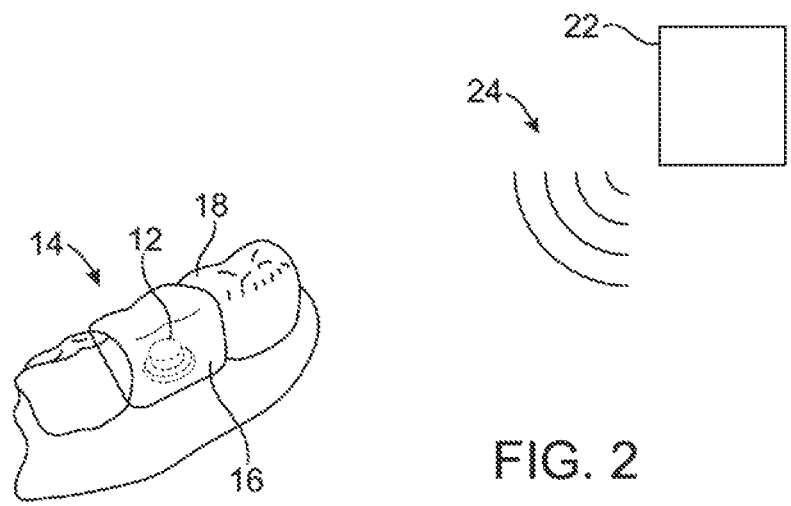
FIG. 2 illustrates a detail perspective view of the oral implant appliance positioned upon the patient's teeth utilizable in combination with a transmitting assembly external to the mouth and wearable by the patient in another variation of the device.

FIG. 2 shows a perspective view of the patient's lower dentition illustrating the hearing aid assembly 14 comprising a removable oral appliance 18 and the electronics and/or transducer assembly 16 positioned along a surface of the assembly 14. In this variation, oral appliance 18 may be positioned on or above screw 12 implanted into the patient's bone or tissue. Moreover, electronics and/or transducer assembly 16 can be fitted inside the oral appliance 18. The figures are illustrative of variations and are not intended to be limiting; accordingly, other configurations and shapes for oral appliance 18 are intended to be included herein.

Generally, the volume of electronics and/or transducer assembly 16 may be minimized so as to be unobtrusive and as comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

In one variation, with assembly 14 positioned upon screw 12, as shown in FIG. 2, an extra-buccal transmitter assembly 22 located outside the patient's mouth may be utilized to receive auditory signals for processing and transmission via a wireless signal 24 to the electronics and/or transducer assembly 16 positioned within the patient's mouth, which may then process and transmit the processed auditory signals via vibratory conductance to the underlying tooth and consequently to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.

Figure 3:
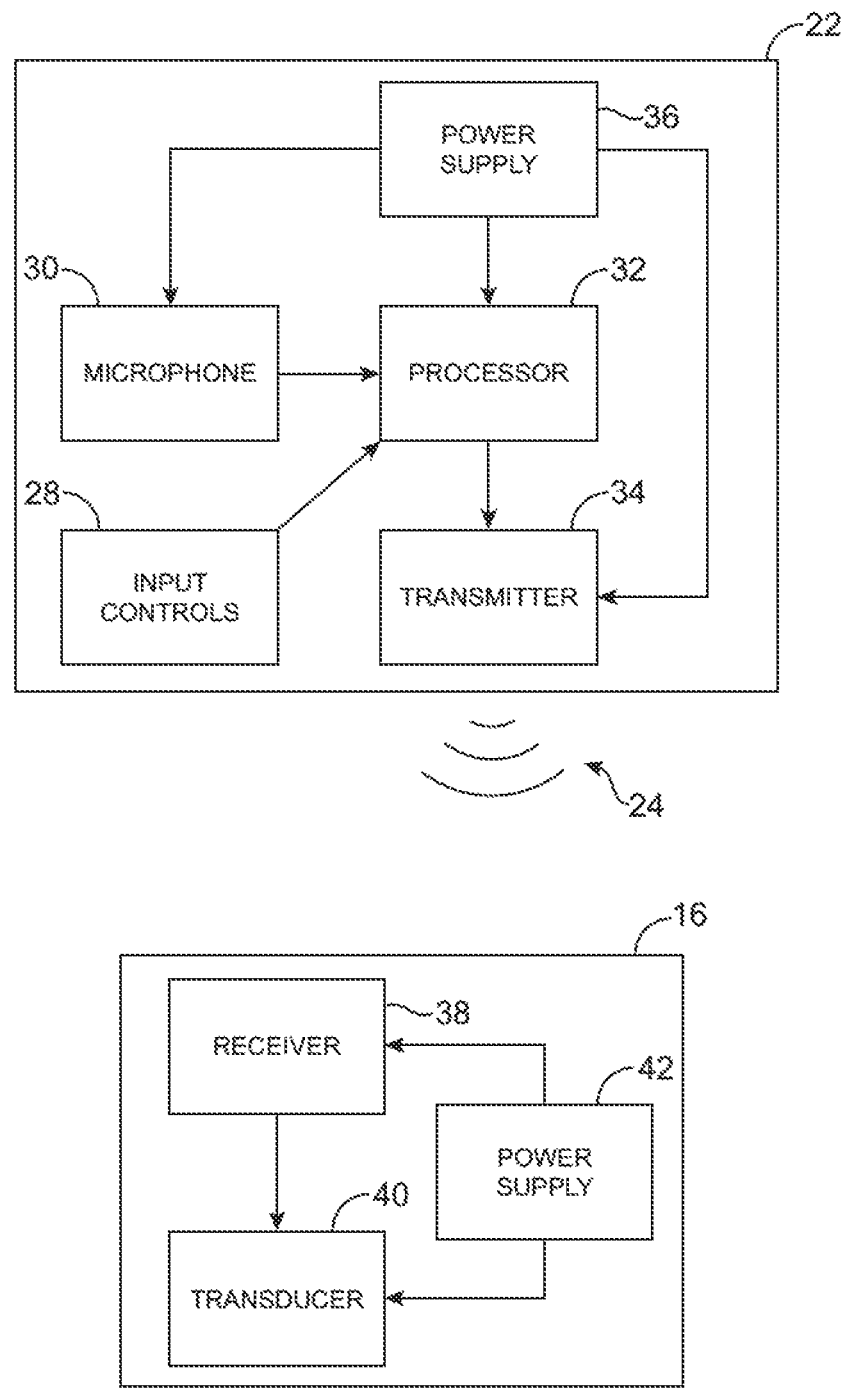
FIG. 3 shows an illustrative, configuration of the individual components in a variation of the oral appliance device having an external transmitting assembly with a receiving and transducer assembly within the mouth.

FIG. 3 illustrates a schematic representation of one variation of hearing aid assembly 14 utilizing an extra-buccal transmitter assembly 22, which may generally comprise microphone 30 for receiving sounds and which is electrically connected to processor 32 for processing the auditory signals. Processor 32 may be connected electrically to transmitter 34 for transmitting the processed signals to the electronics and/or transducer assembly 16 disposed upon or adjacent to the user's teeth. The microphone 30 and processor 32 may be configured to detect and process auditory signals in any practicable range, but may be configured in one variation to detect auditory signals ranging from, e.g., 250 Hertz to 20,000 Hertz.

With respect to microphone 30, a variety of various microphone systems may be utilized. For instance, microphone 30 may be a digital, analog, and/or directional type microphone. Such various types of microphones may be interchangeably configured to be utilized with the assembly, if so desired.

Power supply 36 may be connected to each of the components in transmitter assembly 22 to provide power thereto. The transmitter signals 24 may be in any wireless form utilizing, e.g., radio frequency, ultrasound, microwave, Blue Tooth® (BLUETOOTH SIG, INC., Bellevue, Wash.), etc. for transmission to assembly 16. Assembly 22 may also optionally include one or more input controls 28 that a user may manipulate to adjust various acoustic parameters of the electronics and/or transducer assembly 16, such as acoustic focusing, volume control, filtration, muting, frequency optimization, sound adjustments, and tone adjustments, etc.

The signals transmitted 24 by transmitter 34 may be received by electronics and/or transducer assembly 16 via receiver 38, which may be connected to an internal processor for additional processing of the received signals. The received signals may be communicated to transducer 40, which may vibrate correspondingly against a surface of the tooth to conduct the vibratory signals through the tooth and bone and subsequently to the middle ear to facilitate hearing of the user. Transducer 40 may be configured as any number of different vibratory mechanisms. For instance, in one variation, transducer 40 may be an electromagnetically actuated transducer. In other variations, transducer 40 may be in the form of a piezoelectric crystal having a range of vibratory frequencies, e.g., between 250 to 4000 Hz.

Power supply 42 may also be included with assembly 16 to provide power to the receiver, transducer, and/or processor, if also included. Although power supply 42 may be a simple battery, replaceable or permanent, other variations may include a power supply 42 which is charged by inductance via an external charger. Additionally, power supply 42 may alternatively be charged via direct coupling to an alternating current (AC) or direct current (DC) source. Other variations may include a power supply 42 which is charged via a mechanical mechanism, such as an internal pendulum or slidable electrical inductance charger as known in the art, which is actuated via, e.g., motions of the jaw and/or movement for translating the mechanical motion into stored electrical energy for charging power supply 42.

Figure 4:
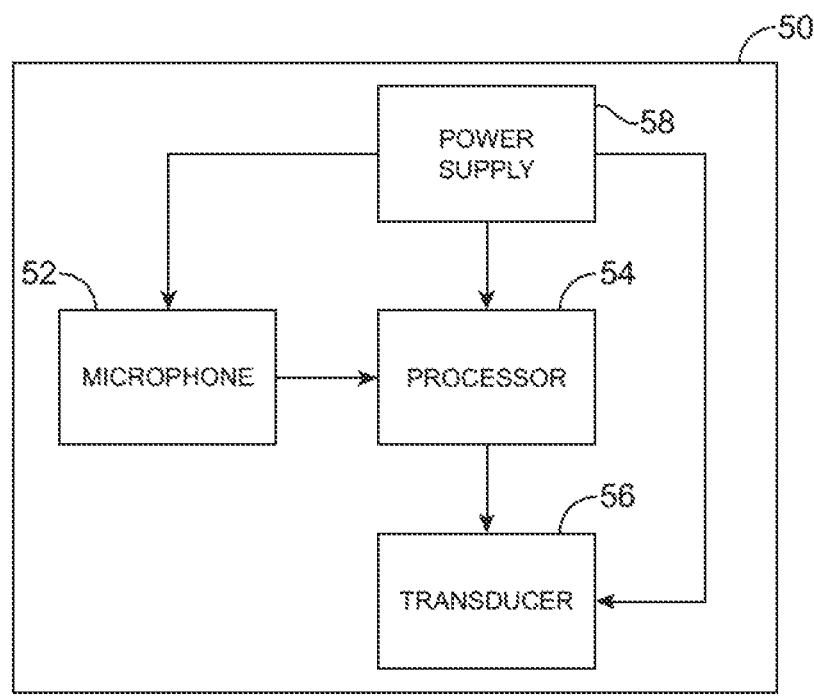
FIG. 4 shows an illustrative configuration of another variation of the device in which the entire assembly is contained by the oral appliance within the user's mouth.

In another variation of assembly 16, rather than utilizing an extra-buccal transmitter, hearing aid assembly 50 may be configured as an independent assembly contained entirely within the user's mouth, as shown in FIG. 4. Accordingly, assembly 50 may include an internal microphone 52 in communication with an on-board processor 54. Internal microphone 52 may comprise any number of different types of microphones, as described above. Processor 54 may be used to process any received auditory signals for filtering and/or amplifying the signals and transmitting them to transducer 56, which is in vibratory contact against the tooth surface. Power supply 58, as described above, may also be included within assembly 50 for providing power to each of the components of assembly 50 as necessary.

In order to transmit the vibrations corresponding to the received auditory signals efficiently and with minimal loss to the tooth or teeth, secure mechanical contact between the transducer and the tooth is ideally maintained to ensure efficient vibratory communication. Accordingly, any number of mechanisms may be utilized to maintain this vibratory communication.

Figure 5A:
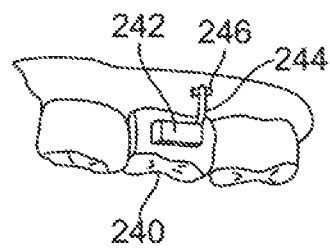
FIGS. 5A and 5B illustrate perspective and side views, respectively, of an oral appliance which may be coupled to a screw or post implanted directly into the underlying bone, such as the maxillary or mandibular bone.
Figure 5B:
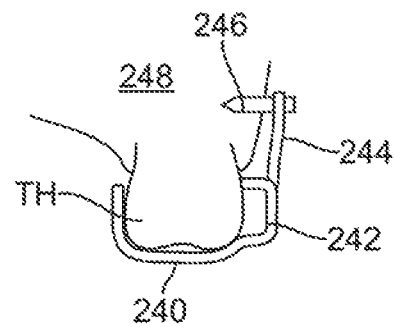

In various embodiments vibrations may be transmitted directly into the underlying bone or tissue structures. As shown in FIG. 5A, an oral appliance 240 is illustrated positioned upon the user's tooth, in this example upon a molar located along the upper row of teeth. The electronics and/or transducer assembly 242 is shown as being located along the buccal surface of the tooth. Rather than utilizing a transducer in contact with the tooth surface, a conduction transmission member 244, such as a rigid or solid metallic member, may be coupled to the transducer in assembly 242 and extend from oral appliance 240 to a post or screw 246 which is implanted directly into the underlying bone 248, such as the maxillary bone, as shown in the partial cross-sectional view of FIG. 5B. As the distal end of transmission member 244 is coupled directly to post or screw 246, the vibrations generated by the transducer may be transmitted through transmission member 244 and directly into post or screw 246, which in turn transmits the vibrations directly into and through the bone 248 for transmission to the user's inner ear.

Figure 5C:
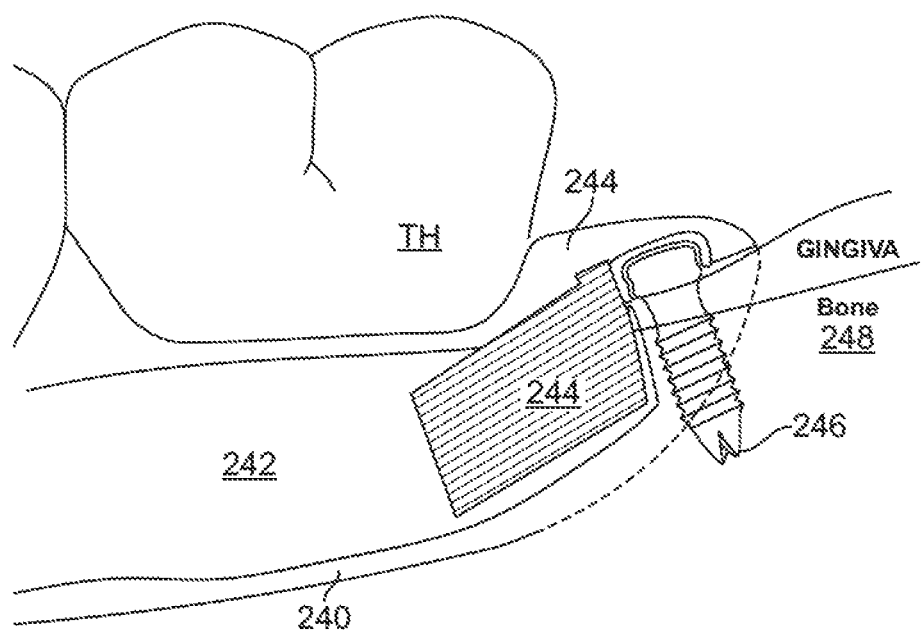
FIGS. 5C and 5D illustrate two additional dental implant embodiments.
Figure 5D:
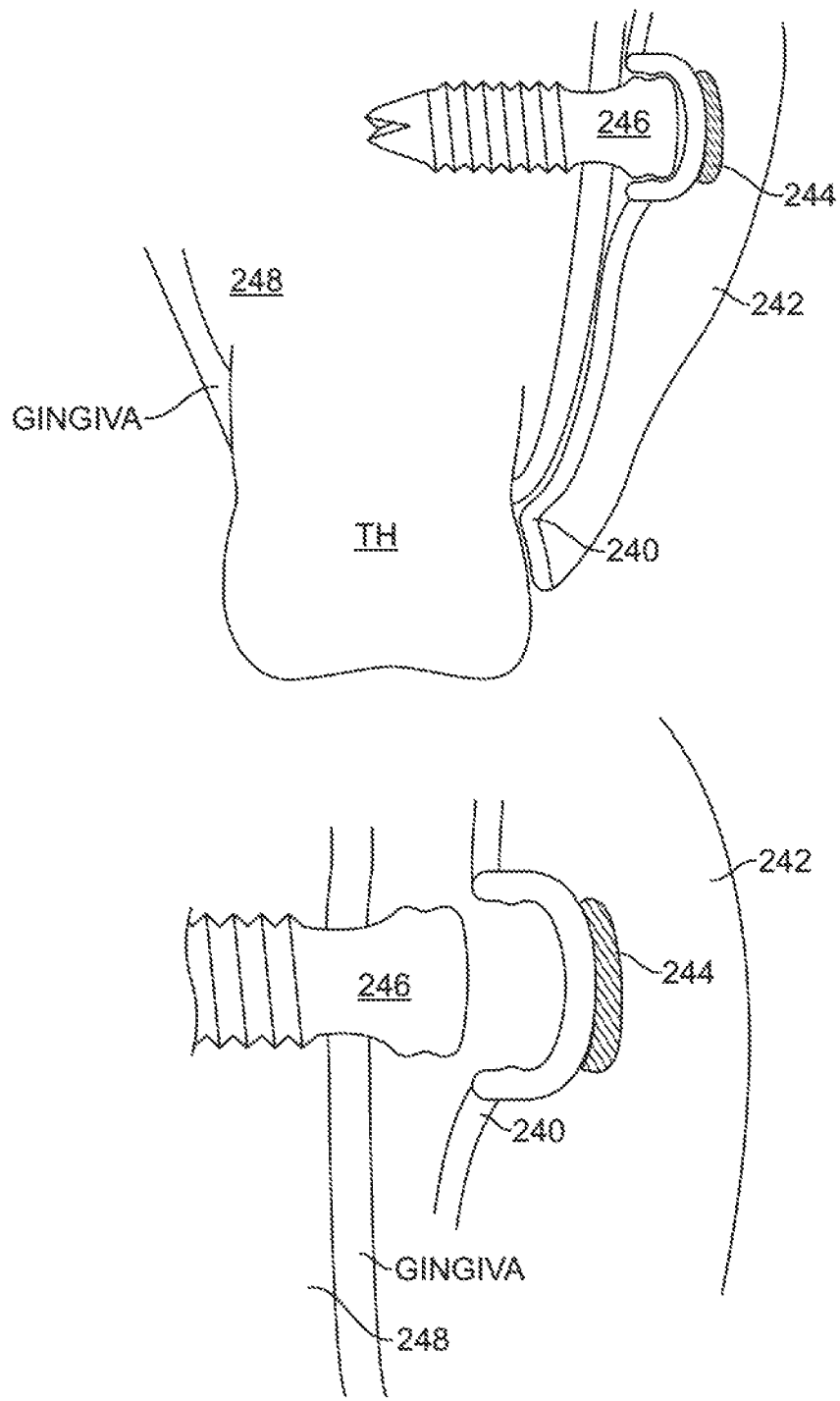

FIGS. 5C and 5D illustrate additional dental implant embodiments. In FIG. 5C, the transducer assembly 242 contains the transmission member 244, which in turn is connected to a snap fit housing 240. The snap fit housing 240 is securely snapped onto an implant 246 which has an exposed head that receives the snap fit housing. The implant head can be an implant abutment that is threaded onto the implant fixture, or directly connected to the implant fixture as one piece. One piece implants avoid the presence of microgaps, while multi-piece implants provide more options for various clinical needs with fewer components. The implant 246 is securely screwed into bone through the gingival 248. The cutting end of the implant may contain cutting edges to facilitate direct implant placement without pre-drilling. The threads of the implant 246 may have constant or progressive thread geometry along the length of the threaded regions of the implant. Sharp edges can be used to promote cutting, and is more effectively utilized towards the apical end of the implant. Rounded square threads are more effective in distributing forces and hence promote osseointegration. For rounded square threads, optimal stress distribution is obtained by controlling the width of each thread (i.e. major diameter minus minor diameter) to be 40-50% of the thread pitch height; and by controlling the thread height (height of the region that defines the major diameter) to be 50% of the thread pitch. Microgrooves may promote soft tissue adaptation to the implant and may be placed in the implant above the threads, and therefore above the crestal bone, in the region where the implant traverses the gingival tissue. The transmucosal component may be constricted sightly to produce platform switching-like effects. The surface texture (e.g. roughness) can dramatically alter biological bone response to the surface, as well as the mechanical advantage due to increased surface area and increased resistance to removal. Sand blasting, acid etching, plasma spraying, nucleation and growth, plasma etching, etc., are well known in the art to produce biocompatible surfaces. Tissue adaptation to the implant has also been shown to be improved with the addition of bioceramics, cell adhesion molecules, and delivery of cytokines, drugs, genes, and growth factors. The surface modification can include altering biological bone response to an implant surface using one of: texturing the implant surface, physically modifying the implant surface, chemically modifying the implant surface, and biologically modifying the implant surface. Texturing is one way to perform physical modification. Other physical modification methods can include sandblasting, laser grinding, milling, among others. Chemical modification of the implant surface can include vapor deposition, plasma etching, acid or base, or providing precursors to growth biocompatible oxides, drugs, vitamin D, among others. Alternatively, biological modifications can be done, including providing cell adhesion molecules (fibronectin, laminin, etc.), extracellular matrix molecules (collagen, figinogen, etc.), cytokines (, peptides (RGD repeats, etc.), growth factors (BMPs, FGFs, VEGF, etc.), for example. Turning now to FIG. 5D, a different way of inserting the implant in FIG. 5C is shown. Whereas FIG. 5C shows a vertically placed implant, similar to the way natural teeth are aligned within the jaw bone, FIG. 5D shows a horizontally place implant. The implant in FIG. 5D may be apical to the roots of the teeth, or placed in between the roots of the teeth. When placed apical to the roots, anatomical features is considered to ensure adequate bone-to-implant contact. For example, the maxillary sinus apical to the maxillary posterior teeth may preclude that type of placement. On the buccal side, short vestibule area may also preclude horizontal placement above the roots of the teeth. In these and other cases, the implant can be placed horizontally, in between the roots of the adjacent teeth, where the maximum implant diameter must consider the width of the periodontal ligament space (0.25-0.3 mm) on each adjacent teeth. The bottom illustration in FIG. 5D shows in more details relationship between the snap fit housing 240 and the implant 246. FIG. 5D also shows the transmission member 244 positioned above the snap fit housing 240 and the head of the implant 246.

For a single implant or screw 246, the snap fit housing 240 is attached to the transmission member 244. For multiple screw embodiments, only one screw is needed for bone conduction, and the snap fit housing for the remaining screws can be attached to the respective screw heads without being connected to the transmission member 244.

Figure 6:
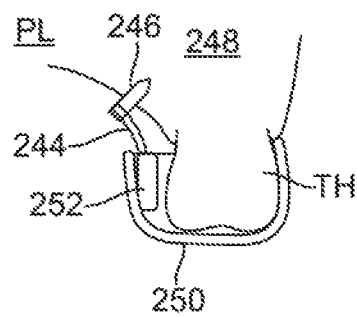
FIG. 6 illustrates another variation in which the oral appliance may be coupled to a screw or post implanted directly into the palate of a patient.

FIG. 6 illustrates a partial cross-sectional view of an oral appliance 250 placed upon the user's tooth TH with the electronics and/or transducer assembly 252 located along the lingual surface of the tooth. Similarly, the vibrations may be transmitted through the conduction transmission member 244 and directly into post or screw 246, which in this example is implanted into the palatine bone PL. Other variations may utilize this arrangement located along the lower row of teeth for transmission to a post or screw 246 drilled into the mandibular bone.

Figure 7A:
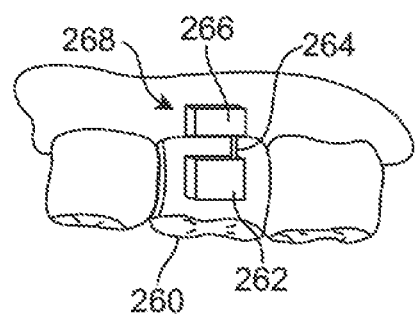
FIGS. 7A and 7B illustrate perspective and side views, respectively, of an oral appliance which may have its transducer assembly or a coupling member attached to the gingival surface to conduct vibrations through the gingival tissue and underlying bone.
Figure 7B:
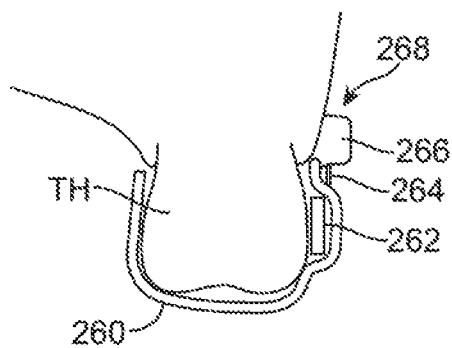

In yet another variation, rather utilizing a post or screw drilled into the underlying bone itself, a transducer may be attached, coupled, or otherwise adhered directly to the gingival tissue surface adjacent to the teeth. As shown in FIGS. 7A and 7B, an oral appliance 260 may have an electronics assembly 262 positioned along its side with an electrical wire 264 extending therefrom to a transducer assembly 266 attached to the gingival tissue surface 268 next to the tooth TH. Transducer assembly 266 may be attached to the tissue surface 268 via an adhesive, structural support arm extending from oral appliance 260, a dental screw or post, or any other structural mechanism. In use, the transducer may vibrate and transmit directly into the underlying gingival tissue, which may conduct the signals to the underlying bone.

Figure 8:
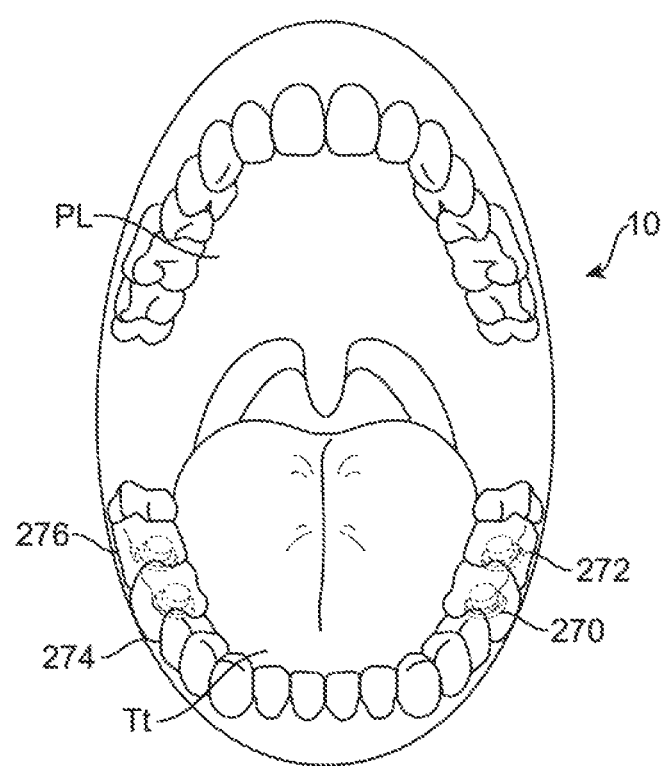
FIG. 8 illustrates an example of how multiple oral appliance hearing aid assemblies or transducers may be placed on multiple teeth throughout the patient's mouth.

For any of the variations described above, they may be utilized as a single device or in combination with any other variation herein, as practicable, to achieve the desired hearing level in the user. Moreover, more than one oral appliance device and electronics and/or transducer assemblies may be utilized at any one time. For example, FIG. 8 illustrates one example where multiple transducer assemblies 270, 272, 274, 276 may be placed on multiple dental implants. Although shown on the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within non-overlapping frequency ranges between each assembly. As mentioned above, each transducer 270, 272, 274, 276 can be programmed or preset for a different frequency response such that each transducer may be optimized for a different frequency response and/or transmission to deliver a relatively high-fidelity sound to the user.

Moreover, each of the different transducers 270, 272, 274, 276 can also be programmed to vibrate in a manner which indicates the directionality of sound received by the microphone worn by the user. For example, different transducers positioned at different locations within the user's mouth can vibrate in a specified manner by providing sound or vibrational queues to inform the user which direction a sound was detected relative to an orientation of the user. For instance, a first transducer located, on a user's left tooth, can be programmed to vibrate for sound detected originating from the user's left side. Similarly, a second transducer located, e.g., on a user's right tooth, can be programmed to vibrate for sound detected originating from the user's right side. Other variations and queues may be utilized as these examples are intended to be illustrative of potential variations.

Figure 9:
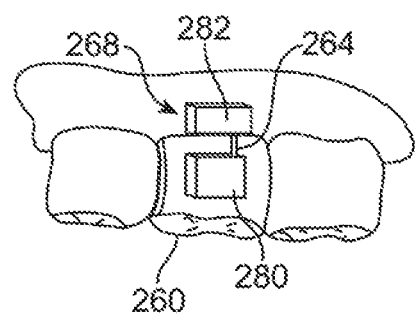
FIG. 9 illustrates a perspective view of an oral appliance (similar to a variation shown above) which may have a microphone unit positioned adjacent to or upon the gingival surface to physically separate the microphone from the transducer to attenuate or eliminate feedback.

In variations where the one or more microphones are positioned in intra-buccal locations, the microphone may be integrated directly into the electronics and/or transducer assembly, as described above. However, in additional variation, the microphone unit may be positioned at a distance from the transducer assemblies to minimize feedback. In one example, similar to a variation shown above, microphone unit 282 may be separated from electronics and/or transducer assembly 280, as shown in FIG. 9. In such a variation, the microphone unit 282 positioned upon or adjacent to the gingival surface 268 may be electrically connected via wire(s) 264.

Figure 10:
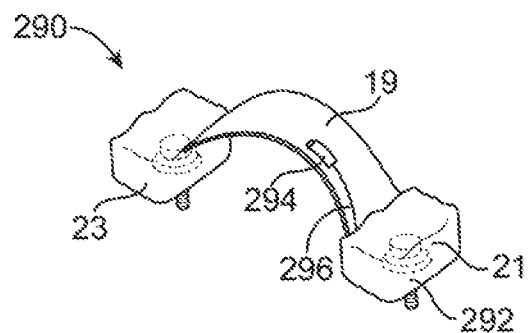
FIG. 10 illustrates another variation of a removable oral appliance supported by an arch and having a microphone unit integrated within the arch.

Although the variation illustrates the microphone unit 282 placed adjacent to the gingival tissue 268, unit 282 may be positioned upon another dental implant, screw implant or another location within the mouth. For instance, FIG. 10 illustrates another variation 290 which utilizes an arch 19 connecting one or more dental implant retaining portions 21, 23, as described above. However, in this variation, the microphone unit 294 may be integrated within or upon the arch 19 separated from the transducer assembly 292. One or more wires 296 routed through arch 19 may electrically connect the microphone unit 294 to the assembly 292. Alternatively, rather than utilizing a wire 296, microphone unit 294 and assembly 292 may be wirelessly coupled to one another, as described above.

Figure 11:
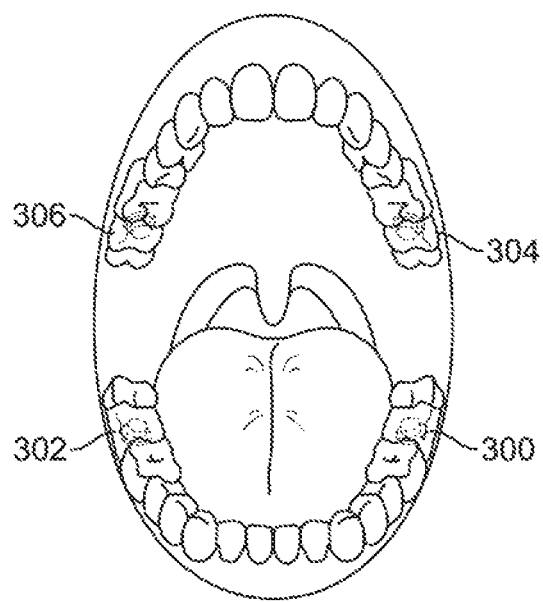
FIG. 11 shows yet another variation illustrating at least one microphone and optionally additional microphone units positioned around the user's mouth and in wireless communication with the electronics and/or transducer assembly.

In yet another variation for separating the microphone from the transducer assembly. FIG. 11 illustrates another variation where at least one microphone 302 (or optionally any number of additional microphones 304, 306) may be positioned within the mouth of the user while physically separated from the electronics and/or transducer assembly 300. In this manner, the one or optionally more microphones 302, 304, 306 may be wirelessly coupled to the electronics and/or transducer assembly 300 in a manner which attenuates or eliminates feedback, if present, from the transducer.

Figure 12A:
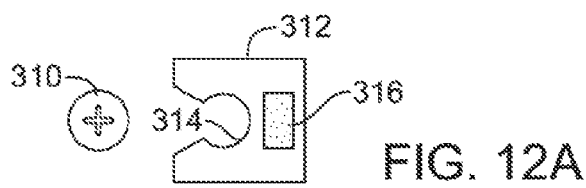
FIGS. 12A, 12B and 12C show various views of one embodiment of an electro-magnetic based attachment to implants for transmission of vibrations to teeth.
Figure 12B:
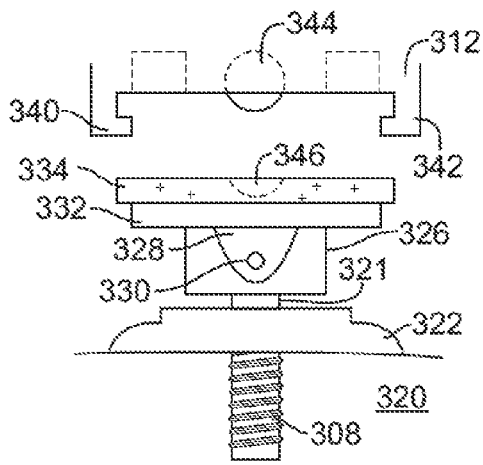
Figure 12C:
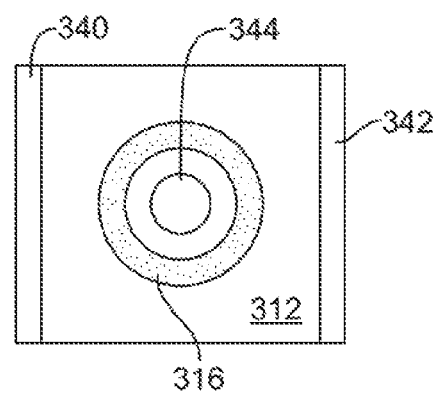

FIGS. 12A, 12B and 12C show various views of one embodiment of an electro-magnetic based attachment to a dental implant for transmission of vibrations to teeth. The dental implant includes an upper portion (implant head) and lower portion (threaded portion) with at least the lower portion assuming a generally tapered and conical shape. While various materials can be used to construct the implant, it is widely recognized that one of the more suitable materials for dental implants is titanium. This is due, in part at least, to the fact that titanium is a very strong and light metal and is highly resistant to corrosion and degradation even though when implanted the implant assumes a position embedded within the alveolar bone structure of a patient.

In one embodiment, the implant can be provided with an anchoring pin or screw that functions to securely anchor the implant within the alveolar bone of the patient. The anchoring pin prevents the implant from rotating of becoming loose when the implant is embedded within the alveolar bone of the patient. The anchoring pin is of the self-tapping type and includes a screw head 310, a smooth shank portion 321, and a threaded self-tapping portion 308. The anchoring pin is inserted downwardly through an access opening and into the throughbore. Once in the throughbore, the screw head 310 is engaged with a turning tool such as a screw driver or Allen wrench that extends through the access opening, and the anchoring pin is turned causing the self-tapping threads 308 to be pulled within bone structure adjacent to the implant. The anchoring, pin further anchors and secures the implant in place and is particularly designed to prevent the implant from rotating or becoming loose under stress or load.

The implant can be utilized without an anchoring pin and can be inserted and stationed within the alveolar bone of a patient by simply screwing the implant into the alveolar bone. In certain cases, the utilization of an anchoring pin may assist in stabilizing and preventing the implant from rotating under load or stress.

FIG. 12A shows a top view of an implant having an implant head or a screw head 310 and a vibratory transducer 312. The vibratory transducer 312 can include a protective housing, or simply can include the electronic components that are covered by a protective seal or coating. The screw head 310 is charged in a predetermined polarity (either north or south polarity). The vibratory transducer 312 is shaped to engage the screw head 310 at opening 314. The vibratory transducer 312 contains a magnet 316 having the end facing the screw head 310 charged in an opposite polarity to the screw head's polarity. In this manner, the transducer 312 and the screw head 310 are strongly attracted to each other to secure the two together. Such tight physical coupling minimizes resonance vibrations that occur if the transducer 312 and the screw head 310 were not attracted to each other.

FIG. 12B shows another means of attachment to the screw head. A screw head 326 is secured to the bone portion 320 when a threaded portion 321 is screwed into the bone portion 320. The screw head 326 supports a base plate 332 through a pivot tab 328 that is secured to the screw head 326 using a rod 330. A top plate 334 is positioned above the base plate 332 and extends beyond the base plate 332 to engage a pair of arms 340-342 positioned on the bottom of the vibratory transducer 312. Additionally, a ball 344 is positioned on the transducer 312 and is spring loaded (not shown) so that the transducer 312 and the ball 344 are adapted to locate a spherical indentation 346 on the top plate 334. During insertion of the transducer 312 into the screw head 310, the ball 344 engages the spherical indentation 346 to properly orient the transducer 312. The magnet 316 encircles the ball spring 344 and opposing magnetic forces secure the screw head 310 to the transducer 312 containing the magnet 316. During insertion, the ball 344 drops into the spherical orientation 346 to allow the transducer 312 to be properly positioned over the screw head 310.

The vibratory transducer 312 may generally include a microphone for receiving sounds and which is electrically connected to a processor for processing the auditory signals. The processor may be electrically connected to an antenna for receiving wireless communication signals. e.g., input control signals from an external remote control and/or other external sound generating devices, e.g., cell phones, telephones, stereos, MP3 players, and other media players. The microphone and processor may be configured to detect and process auditory signals in any practicable range, but may be configured in one variation to detect auditory signals ranging from, e.g., 250 Hertz to 20,000 Hertz. The detected and processed signals may be amplified via amplifier, which increases the output levels for vibrational transmission by transducer 312 into the adjacent, or otherwise coupled, bone structure 322 such as a patient's tooth or teeth.

With respect to microphone, a variety of various microphone systems may be utilized. For instance, microphone may be a digital, analog, piezoelectric, and/or directional type microphone. Such various types of microphones may be interchangeably configured to be utilized with the assembly, if so desired.

The signals transmitted may be received by electronics and/or transducer assembly via a receiver, which may be connected to an internal processor for additional processing of the received signals. The received signals may be communicated to transducer 312, which may vibrate correspondingly against a surface of the tooth to conduct the vibratory signals through the tooth and bone and subsequently to the middle ear to facilitate hearing of the user. Transducer 312 may be configured as any number of different vibratory mechanisms. For instance, in one variation, transducer 312 may be an electromagnetically actuated transducer. In other variations, transducer 312 may be in the form of a piezoelectric crystal having a range of vibratory frequencies, e.g., between 250 to 20,000 Hz.

The implant process starts after a tooth extraction cavity has healed and closed. The first step is to determine the proper size implant from a standard kit or standard group of implants. Since the extraction cavity has now become closed and healed, the particular implant is selected based on the size and condition of the implant site. In any event, after the proper implant has been selected, the next step entails drilling a receiving cavity through the gum and alveolar bone of the patient at the implant site. The particular drill is selected based on the optimum size implant selected from the standard group of implants. But in any event, a drill guide is utilized and the selected drill bit is directed downwardly through the drill gauge into the alveolar bone of the patient creating an implant cavity. Once the bore has been created then the next step is to utilize a selected reamer, again based on the implant selection. This also occurs after a tooth has been extracted and it is the intent of the dentist of oral surgeon to immediately set the implant. In either case, a select reamer is chosen based on the optimum size of the implant to be used. A reamer guide can be secured about the extraction cavity or the cavity formed by the drill. The reamer is preferably of a conical of tapered shape and would generally conform to the shape of the original root structure of the extracted tooth. The cavity is reamed and the extraneous material resulting from the reaming is removed. Thereafter, as discussed herein before, the implant is inserted within the reamed cavity and anchored within the alveolar bone. Next, the anchoring pin or screw is extended through the throughbore and screwed into the alveolar bone adjacent the implant. This couples the implant to the alveolar bone and prevents rotation and loosening.

Complete osseointegration, i.e. the dynamic interaction of living bone with a biocompatible implant without an intervening soft tissue layer, is preferred but not essential in all cases. When the bone quality is sufficient (abundant bone volume and high hone density), immediate loading or delayed loading (weeks) may be considered since the force parameters involved for this application are very low. There may be the possibility that selected force parameters can promote the bone healing.

When the bone quality is insufficient (inadequate bone volume or density), then more healing time may be required for establishing implant stability. In such cases, after the implant has been placed, the implant site is closed in order that the same can heal for a period of time. A temporary cap can be used, or the gingival flap may be returned across the top of the implant so as to close the same. However, it is also possible to leave the implant head exposed during the healing period, similar to the ITI dental implant concept. Thereafter, osseointegration occurs, and bone structure remodels and heals in intimate contact with the implant without an intervening soft tissue layer. The time for complete osseointegration can vary from approximately 3 to 12 months depending on the age of the patient and other factors. However, due to the force parameters of this application, the implant may be used without complete osseointegration. It is likely that 1-3 months may be adequate for many cases. If a flap was placed and healing was allowed to occur under the mucosal tissues, then after the appropriate healing time the dentist or oral surgeon can return to the implant site and surgically opens the gingival flap and attach a transmucosal abutment for the vibratory transducer 312 to be mounted.

FIGS. 13A, 13B, 13C and 13D show various embodiments of mechanical based attachments to implants for transmission of vibrations to teeth. A dental implant in FIG. 13A includes a threaded portion 308 that is apical to the gum line 320 and an implant head or screw head 326 that extends above the hone region 320. A vibratory transducer 340 engages the screw head 326 to transmit or conduct sound through the bone region 320. The vibratory transducer 340 has a plurality of springs 356 that provide spring-loaded forces to cause balls or tabs 358 to securely engage the screw head 326. In one embodiment, the screw head 326 has a plurality of recesses 327 to engage the balls or tabs 358.

Figures 13A, 13B:
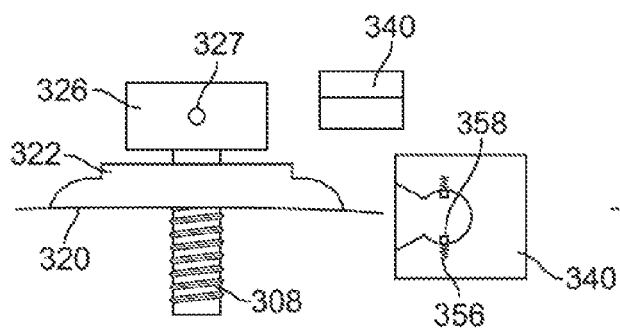
FIGS. 13A, 13B, 13C and 13D show various embodiments of mechanical based attachments to implants for transmission of vibrations to teeth.
Figure 13C:
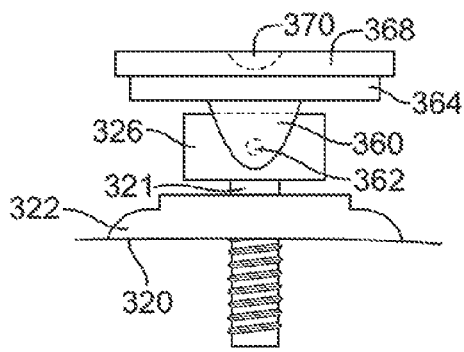
Figure 13D:
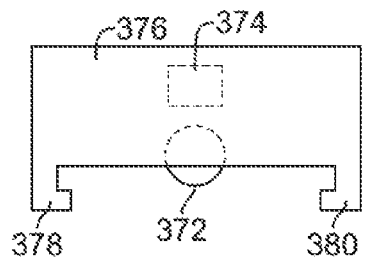

Referring now to FIG. 13B, another embodiment to mechanically attach the vibratory transducer 340 is shown. In this embodiment, the implant head or screw head 326 has an opening therethrough to receive one arm of a clip 352. The clip 352 has a supporting surface 334 that engages a top plate 346. In one embodiment, the top plate 346 has a ball 344 that cooperates with a spherical indentation on the top place 334 to properly position the transducer 340 on the top plate 346. The implant head or screw head 326 supports a base plate 364 through a pivot tab 360 that is secured to the screw head 326 using a second screw or rod 362. A top plate 368 is positioned above the base plate 364 and extends beyond the base plate 364 to engage a pair of arms 378-380 positioned on the bottom of the vibratory transducer 376. Additionally, a ball 372 is positioned on the vibratory transducer 376 and is spring loaded through spring 374 so that the vibratory transducer 376 and the ball 372 are adapted to locate a spherical indentation 370 on the top plate 368. During insertion or installation of the vibratory transducer 376 into the screw head 326, the ball 372 engages the spherical indentation 370 to properly orient the vibratory transducer 376.

Figure 14A:
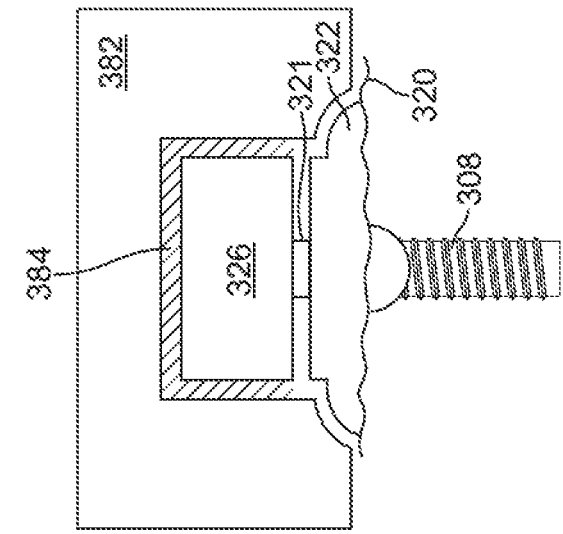
FIGS. 14A and 14B show various views of one embodiment of a chemical based attachment to implants for transmission of vibrations to teeth.
Figure 14B:
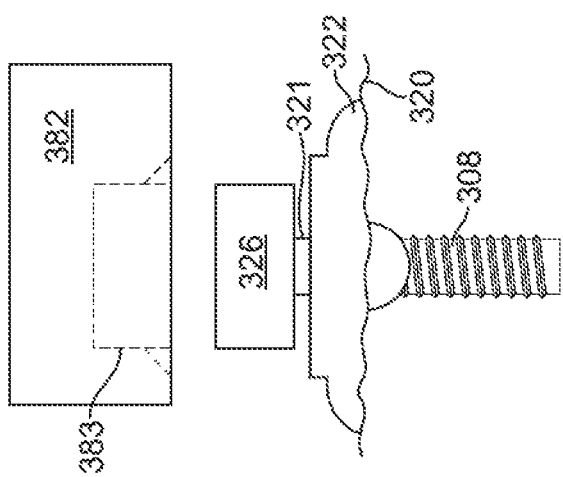

In sum, the base plate 322 has a rod 352 or 330 attached to the base plate 322. The rod 352 or 330 slides into the hole in the screw head 312 or 326. The transducer portion then attaches to that base plate either with a magnet as in FIG. 12B and FIG. 12C or mechanically as in FIG. 13B or FIG. 13C. FIGS. 14A and 14B show two chemical embodiments for attaching the vibrational transducer to the screw head 312 or 326.

FIGS. 14A and 14B show various views of one embodiment of a chemical based attachment to implants for transmission of vibrations to teeth. FIG. 14A shows the vibratory transducer 382 prior to mounting on the implant head or screw head 326, while FIG. 14B shows the completed transducer and implant head of screw head assembly. An implant Lead or screw implant in FIG. 32A includes a threaded portion 308 that is below the gum line 320 and a screw head 326 that extends above the bone region 320. A vibratory transducer 382 engages the screw head 326 to transmit or conduct sound through the bone region 320. The vibratory transducer 382 has a recess 383 that engages the screw head 326. To secure the transducer 382 to the screw head 326, an adhesive layer 384 is provided at an interface between the transducer 382 and the screw head 326.

The implant can be used to treat tinnitus or stuttering. For stuttering, the implant can play frequency shifted and delayed version of the sound directed at the patient and this delayed playback stops the patient's stuttering. For example, the sound is frequency shifted by about 500 Hz and the auditory feedback can be delayed by about 60 ms. The self-contained dental implant assists those who stutter. With the device in place, stuttering is reduced and speech produced is judged to be more natural than without the device.

The implant can treat tinnitus, which is a condition in which sound is perceived in one or both ears or in the head when no external sound is present. Such a condition may typically be treated by masking the tinnitus via a generated noise or sound. In one variation, the frequency or frequencies of the tinnitus may be determined through an audiology examination to pinpoint the range(s) in which the tinnitus occurs in the patient. This frequency or frequencies may then be programmed into a removable oral device which is configured to generate sounds which are conducted via the user's tooth or bones to mask the tinnitus. One method for treating tinnitus may generally comprise masking the tinnitus where at least one frequency of sound (e.g., any tone, music, or treatment using a wide-hand or narrow-band noise) is generated via an actuatable transducer positioned against at least one tooth such that the sound is transmitted via vibratory conductance to an inner ear of the patient, whereby the sound completely or at least partially masks the tinnitus perceived by the patient. In generating a wide-band noise, the sound level may be raised to be at or above the tinnitus level to mask not only the perceived tinnitus but also other sounds. Alternatively, in generating a narrow-band noise, the sound level may be narrowed to the specific frequency of the tinnitus such that only the perceived tinnitus is masked and other frequencies of sound may still be perceived by the user. Another method may treat the patient by habituating the patient to their tinnitus where the actuatable transducer may be vibrated within a wide-band or narrow-band noise targeted to the tinnitus frequency perceived by the patient overlayed upon a wide-frequency spectrum sound. This wide-frequency spectrum sound, music, may extend over a range which allows the patient to periodically hear their tinnitus through the sound and thus defocus then attention to the tinnitus. In enhancing the treatment for tinnitus, a technician, audiologist, physician, etc., may first determine the one or more frequencies of tinnitus perceived by the patient. Once the one or more frequencies have been determined, the audiologist or physician may determine the type of treatment to be implemented, e.g., masking or habituation. Then this information may be utilized to develop the appropriate treatment and to compile the electronic treatment program file which may be transmitted, e.g., wirelessly, to a processor coupled to the actuatable transducer such that the transducer is programmed to vibrate in accordance with the treatment program.

In use, an implant containing the transducer may be placed against one or more teeth of the patient and the transducer may be actuated by the user when tinnitus is perceived to generate the one or more frequencies against the tooth or teeth. The generated vibration may be transmitted via vibratory conductance through the tooth or teeth and to the inner ear of the patient such that each of the frequencies of the perceived tinnitus is masked completely or at least partially. The oral implant may be programmed with a tinnitus treatment algorithm which utilizes the one or more frequencies for treatment. This tinnitus treatment algorithm may be uploaded to the oral appliance wirelessly by an external programming device to enable the actuator to vibrate according to the algorithm for treating the tinnitus. Moreover, the oral appliance may be used alone for treating tinnitus or in combination with one or more hearing aid devices for treating patients who suffer not only from tinnitus but also from hearing loss.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. An apparatus for transmitting vibrations, comprising:
    an implant having an implant head and a threaded portion adapted to be positioned below a gum line;
    a housing which is sized for placement within a mouth of the patient;
    an actuatable transducer comprised of a piezoelectric material and disposed within or upon the housing, wherein the transducer is removably coupled to the implant head such that when connected the transducer is in vibratory communication with the implant head and when removed the transducer is not in communication with the implant head; and
    at least one microphone in communication with the transducer.

2. The apparatus of claim 1 further comprising a piezoelectric microphone in communication with the apparatus.

3. The apparatus of claim 1 wherein the at least one microphone is external to the mouth of the patient.

4. The apparatus of claim 3 wherein the at least one microphone is configured to be worn by the patient.

5. The apparatus of claim 3 wherein the at least one microphone has a form selected from the group consisting of a watch, necklace, lapel, phone, and belt-mounted device.

6. The apparatus of claim 1 further comprising a charger for charging the transducer.

7. The apparatus of claim 1 wherein the housing is coupled to the implant head through one of: an electro-magnetic coupling to the implant head, a mechanical coupling to the implant head, a chemical coupling to the implant head.

8. The apparatus of claim 1 further comprising an electronic assembly disposed within or upon the housing and which is in communication with the transducer.

9. The apparatus of claim 8 wherein the electronic assembly is encapsulated within the housing.

10. The apparatus of claim 8 wherein the electronic assembly further comprises a power supply in electrical communication with the transducer.

11. The apparatus of claim 8 wherein the electronic assembly further comprises a processor in electrical communication with the transducer.

12. The apparatus of claim 8 wherein the electronic assembly further comprises a receiver in wireless communication with an externally located transmitter assembly.

13. The apparatus of claim 1 wherein the actuatable transducer is in vibratory communication with a surface of the implant head via an adhesive for maintaining the transducer in contact with the surface.

14. The apparatus of claim 1 wherein the housing comprises a ball adapted to be seated in an indentation above the implant head.

15. The apparatus of claim 1 wherein the implant head is charged with a first magnetic polarity and the housing is charged with an opposite magnetic polarity.

16. The apparatus of claim 15 further comprising at least one biasing element positioned adjacent to the transducer such that the biasing element maintains the transducer against the implant head via a biasing force.

17. The apparatus of claim 16 wherein the at least one biasing element comprises a spring.

18. The apparatus of claim 1 wherein the housing is inserted into the implant head.

19. The apparatus of claim 18 further comprising a U-shaped clip to mount the housing to the implant head.

20. The apparatus of claim 1 wherein the housing is secured to the implant head using a screw.

* * * * *